(12) United States Patent
Katsevich et al.

(10) Patent No.: US 11,406,344 B2
(45) Date of Patent: Aug. 9, 2022

(54) MOTION ESTIMATION AND COMPENSATION IN CONE BEAM COMPUTED TOMOGRAPHY (CBCT)

(71) Applicants: University of Central Florida Research Foundation, Inc., Orlando, FL (US); iTomography Corporation, Barker, TX (US)

(72) Inventors: Alexander Katsevich, Oviedo, FL (US); Michael Frenkel, Barker, TX (US); Seongjin Yoon, Houston, TX (US)

(73) Assignees: University of Central Florida Research Foundation, Inc., Orlando, FL (US); iTomography Corporation, Barker, TX (US)

( * ) Notice: Subject to any disclaimer, the term of this patent is extended or adjusted under 35 U.S.C. 154(b) by 254 days.

(21) Appl. No.: 16/740,864

(22) Filed: Jan. 13, 2020

(65) Prior Publication Data

US 2020/0222019 A1 Jul. 16, 2020

Related U.S. Application Data

(60) Provisional application No. 62/791,729, filed on Jan. 11, 2019.

(51) Int. Cl.
*A61B 6/00* (2006.01)
*A61B 6/03* (2006.01)
*G06T 11/00* (2006.01)
*G06T 7/20* (2017.01)

(52) U.S. Cl.
CPC ............ *A61B 6/5264* (2013.01); *A61B 6/032* (2013.01); *A61B 6/4085* (2013.01); *G06T 7/20* (2013.01); *G06T 11/008* (2013.01); *G06T 2207/10081* (2013.01); *G06T 2210/41* (2013.01)

(58) Field of Classification Search
CPC .................. G06T 1/0021; G06T 1/005; G06T 2201/0063; G06T 11/006; G06T 11/008; G06T 2207/10081; G06T 2210/41; G06T 2211/424; G06T 7/20; G09C 5/00; A61B 6/03; A61B 6/032; A61B 6/4085; A61B 6/5229; A61B 6/5264; A61N 2005/1061
See application file for complete search history.

(56) References Cited

U.S. PATENT DOCUMENTS

2014/0029824 A1   1/2014   Shi et al.
2016/0210741 A1   7/2016   Brendel et al.

OTHER PUBLICATIONS

Zhang et al., High quality 4D cone-beam CT reconstruction using motion-compensated total variation regularization, Phys. Med. Biol. 62 (2017) 3313-3329.

(Continued)

*Primary Examiner* — Manuchehr Rahmjoo
(74) *Attorney, Agent, or Firm* — Molly L. Sauter; Smith & Hopen, P.A.

(57) ABSTRACT

In various embodiments, the present invention provides an improved system and method for motion estimation and motion compensation in cone beam computer tomography (CBCT). The present invention utilizes a method for alternating minimization between volume and motion sub-iterations and results in an improved system and method for motion estimation and compensation in CBCT.

25 Claims, 5 Drawing Sheets

(56) References Cited

OTHER PUBLICATIONS

Lucka et al., Enhancing Compressed Sensing 4D Photoacoustic Tomography by Simultaneous Motion Estimation, arXiv: 1802.05184v3 (2018).
Burger et al., A variational reconstruction method for undersampled dynamic x-ray tomography based on physical motion models, Inverse Problems 33 (2017) 124008 (24pp).
Burger et al., A Variational Model for Joint Motion Estimation and Image Reconstruction, Siam J. Imaging Sciences (2018) vol. 11, No. 1, pp. 94-128.
Brehm et al., Self-adapting cyclic registration for motion-compensated cone-beam CT in image-guided radiation therapy, Medical Physics 39 (12), Dec. 2012.
Brehm et al., Artifact-resistant motion estimation with a patient-specific artifact mode for motion-compensated cone-beam CT, Med. Phys. 40 (10), Oct. 2013.
Zhong et al., 4D cone-beam CT reconstruction using multi-organ meshes for sliding motion modeling, Phys Med Biol. Feb. 2016. 7; 61(3):996-1020.
International Search Report and Written Opinion dated Apr. 16, 2020 for corresponding PCT International Application No. PCT/US20/13290.

MOTION ESTIMATION AND COMPENSATION IN CONE BEAM COMPUTED TOMOGRAPHY (CBCT)

CROSS-REFERENCE TO RELATED APPLICATIONS

This application claims priority to currently U.S. Provisional Patent Application No. 62/791,729 filed on Jan. 11, 2019 and entitled "Motion Estimation and Compensation in Cone Beam Computed Tomography (CBCT)", the entirety of which is incorporated herein by reference.

BACKGROUND OF THE INVENTION

Accuracy of Cone Beam Computed Tomography (CBCT) images used in radiation treatment of disease sites in the human body is affected by motion artifacts, such as blurring and streaking. These undesirable motion artifacts can result in imprecise patient positioning and unnecessary irradiation of healthy tissue. Other applications in which motion impacts image quality exist as well, such as dental CBCT. Additionally, CBCT scans are generally much slower than conventional clinical CT scans and therefore are very susceptible to motion artifacts. The term 'motion' herein includes both the motion in the conventional sense of the term, but also 'deformation', e.g. as the inner organs are deforming when the person is breathing.

State-of-the-art reconstruction algorithms cannot accurately estimate the motion and compensate for the motion in cases where the region being imaged has mostly low-contrast features, as is commonly the case with CBCT abdomen imaging.

Accordingly, there exists a need for a practical reconstruction algorithm that is more accurate than the current state of the art. Accordingly, what is needed in the art is an improved system and method for motion estimation and compensation in CBCT that exceeds those currently known in the art.

SUMMARY OF INVENTION

In various embodiments, the present invention provides an improved system and method for Four-Dimensional Cone-Beam CT (CBCT) that may be utilized for locating disease (e.g., tumors) prior to the delivery of radiation treatment.

In one embodiment, the present invention provides a method for motion estimation and compensation using X-ray projection scan data. The method includes, acquiring tomographic projection data of a moving object of interest and sorting the projection data according to the motion phase to generate phase-sorted projection data. The method further includes, loading the phase-sorted projection data, initializing a global iteration counter, updating one or more regularization parameters, based upon the phase-sorted projection data, performing a volume sub-iteration of the phase-sorted projection data using the one or more regularization parameters and performing a motion sub-iteration of the phase-sorted projection data using the one or more regularization parameters. Additionally, if the global iteration counter is not equal to a total number of global iteration steps, the method continues by incrementing the global iteration counter and iteratively repeating the steps of updating the one or more regularization parameters, performing volume sub-iteration and performing motion sub-iteration until the global iteration counter is equal to the total number of global iteration steps to estimate the motion of the object of interest during the scan and reconstruct the object.

The result of the final motion sub-iteration of the method can then be used to perform a separate motion compensated reconstruction of an image of the object of interest using the estimated motion of the object of interest.

In the present invention, the volume sub-iteration and the motion sub-iteration are executed independently. Also, in this embodiment, the motion sub-iteration consists of estimating phase Motion Vector Fields (MVFs) between phase volume images. When referring to MVFs, the word 'velocity' may also be used The volume sub-iteration of the global iteration process further includes, resetting Nesterov's parameters, setting a volume sub-iteration counter to zero, computing a volume preconditioner, computing a volume gradient of data fidelity, computing a volume gradient of regularizer, computing a volume gradient of volume-velocity constraint, also referred to as the optical flow constraint (OFC), performing a Nesterov update. Additionally, if the volume sub-iteration counter is not equal to a total number of volume sub-iteration steps, the method continues by incrementing the volume sub-iteration counter and iteratively repeating the steps of computing a volume preconditioner, computing a volume gradient of data fidelity, computing a volume gradient of regularizer, computing a volume gradient of the OFC and performing a Nesterov update until the volume sub-iteration counter is equal to the total number of volume sub-iteration steps.

The motion sub-iteration of the global iteration process further includes, resetting Nesterov's parameters, setting a motion sub-iteration counter to zero, computing a velocity preconditioner, computing a velocity gradient of the OFC, computing a velocity gradient of regularizer, subtracting a mean and setting stationary object velocity to zero, performing a Nesterov update. Additionally, if a difference between consecutive sub-iteration values of the functional being minimized is not lower than a specified threshold value, the method continues by incrementing the motion sub-iteration counter and iteratively repeating the steps of computing a velocity preconditioner, computing a velocity gradient of the OFC, computing a velocity gradient of regularizer, subtracting a mean and setting stationary object velocity to zero and performing a Nesterov update until the difference between consecutive sub-iteration values of the functional being minimized is lower than the specified threshold value.

In one embodiment, the one or more regularization parameters may be updated monotonically. In an additional embodiment, the one or more regularization parameters, for example the OFC strength, may be updated non-monotonically.

In an additional embodiment, the method may use a global in time deformation function as a primary way to describe motion instead of MVFs. In this case, the method may further include modifying the OFC to use MVFs. These MVFs is a secondary way to describe motion, since they are derived from the motion function (the primary way). The MVFs are described on a regular grid during volume sub-iterations to remove speckle artifacts.

This invention is applicable to virtually all radiotherapy (for cancer treatment) CBCT systems, including but not limited to, dental CT systems and other types of CBCT scanners where data acquisition is relatively slow. The invention is additionally applicable to various other modalities and scanning equipment, including, but not limited to clinical Computed Tomography ("CT"), industrial CT, flat panel CT (e.g., C-arms), x-ray diffraction and x-ray based imaging equipment. The inventive concepts can also be applied to other imaging techniques that are not based on x-ray imaging.

The present invention provides for improved image quality compared with known state-of-the-art imaging systems, particularly when imaging complicated low-contrast anatomy, such as in the abdomen of a patient.

BRIEF DESCRIPTION OF THE FIGURES

For a fuller understanding of the invention, reference should be made to the following detailed description, taken in connection with the accompanying drawings, in which.

DETAILED DESCRIPTION OF THE INVENTION

Motion of an object of interest commonly occurs during an imaging scan, such as the natural breathing motion of a patient during a computed tomography (CT) imaging of the patient's abdomen. In various embodiments, the present invention provides a system and method for estimating and compensating for this motion during the reconstruction of the image from the projection data acquired by the CT scanner.

Figure 1:
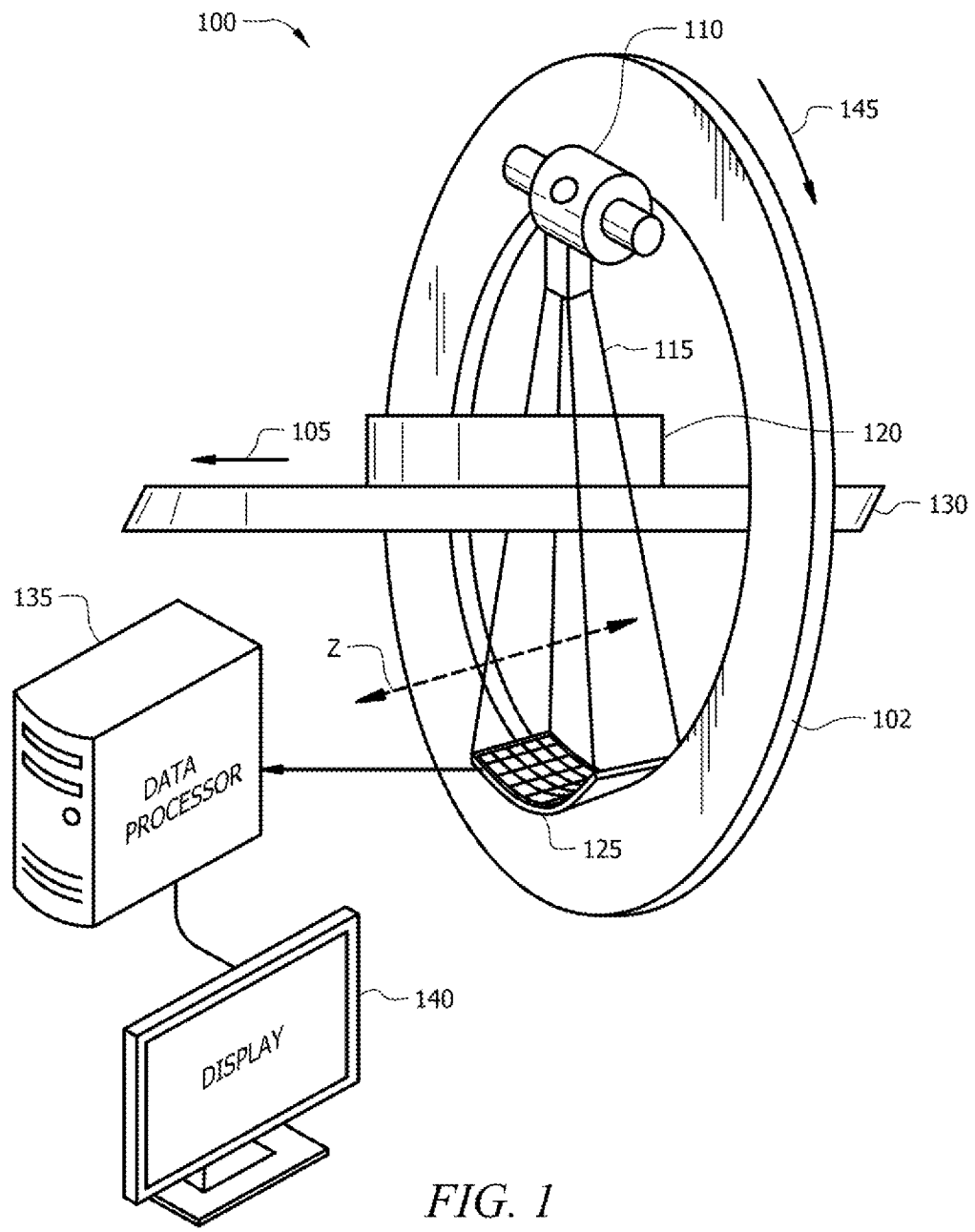
FIG. 1 is an illustration of an exemplary helical computer tomography (CT) scanner, in accordance with an embodiment of the present invention.

FIG. 1 illustrates an exemplary embodiment of a helical CT scanner system 100 according to the present invention. This embodiment is intended to be exemplary and the present invention will be described as relating to medical imaging. However, this is not intended to be limited and various embodiments of the present invention may also be used for other purposes, such as baggage scanning for security and material analysis. Additionally, while a circular CT scanner system is illustrated numerous other scanning devices for collecting projection data are within the scope of the present invention.

As shown in FIG. 1, a circular CT scanner system 100 includes a gantry 102 which is rotatable around a rotational axis 105. The gantry 102 carries a radiation source 110 that forms a cone shaped radiation beam 115. The radiation beam 115 emitted from the radiation source 110 is focused on an object of interest 120 positioned in the center of the gantry 102. A radiation detector 125 is positioned on the gantry 102 opposite from the radiation source 110. The radiation detector 125 comprises a plurality of detector elements for measuring the intensity of the cone shaped radiation beam 115 after it passes through the object of interest 120.

During a scan of the object of interest 120, the radiation source 110 and the radiation detector 125 are rotated with the gantry 102 in a direction indicated 145. The object of interest 120 is additionally positioned on a stationary table 130.

Following the circular scanning of the object of interest 120, the radiation detector 125 provides the collected helical CT scan data to a data processor 135. The data processor 135 is adapted for reconstructing an image from the measurements provided by the radiation detector 125. The image generated by the data processor 135 may then be provided to a display 140 for subsequent viewing.

The data processor 135 is additionally adapted to perform motion estimation and motion compensation to correct for motion in the scan data provided by the radiation detector 125. Motion estimation and compensation may be performed by the data processor 135 as detailed below.

Throughout the detailed description of the invention, the following notations will be used:

$i_q$ qth axis volume grid index
$j_q$ axis velocity grid index
k detector grid index
m source position (projection data) index
$n_g$ global iteration step index
$n_s$ sub-iteration step index
p phase bin index
q spatial coordinate axis index
K total number of detector pixels
M total number of source positions (projection data)
N total number of volume voxels
$\tilde{N}$ total number of velocity voxels
$N_g$ total number of global iteration steps
$N_p$ total phase of bins
$N_q$ total number of volume voxels along qth axis
$\tilde{N}_q$ total number of velocity voxels along qth axis
$N_s$ total number of volume sub-iteration steps
$\tilde{N}_s$ total number of velocity sub-iteration steps In the method of the present invention, the reconstruction volume grid is given by:

$$\vec{x}_i = (h_1 i_1, h_2 i_2, h_3 i_3), i = (i_1, i_2, i_3), \text{ for } 0 \le i_q < N_q, q=1,2,3. \quad (1.1)$$

If the values of a function $f$ are given on the grid (1.1): $f_i = f(\vec{x}_i)$, then the interpolated function becomes:

$$f(\vec{x}) \approx \sum_i f_i \varphi_h(\vec{x} - \vec{x}_i). \quad (1.2)$$

The deformation (or, 'motion') of the object is described by the function $\vec{\psi}(s, \vec{x})$. Here s is time of phase point of a breathing cycle of a patient being imaged.

$$\vec{y} = \vec{\psi}(s, \vec{x}), \quad (1.3)$$

The Equation (1.3) means that the physical point, which at current time s is located at $\vec{x}$, was located at $\vec{y}$ at reference time $s_{ref}$. It is assumed, of course, that $\vec{\psi}(s_{ref}, \vec{x}) = \vec{x}$. Hence, the dynamic attenuation coefficient is given by:

$$f(s, \vec{x}) = f_0(\vec{\psi}(s, \vec{x})), \quad (1.4)$$

where $f_0(\vec{x})$ is the spatial distribution of the attenuation coefficient at reference time.

Additionally, the linear interpolation kernel is used for volume grid ($\varphi_h$), and the cubic B-spline kernel for the motion grid ($\varphi_h$). An exact interpolation of the tri-cubic B-spline is also used for volume-to-motion grid transformation.

To describe the motion function, a motion grid is introduced:

$$\vec{m}_j = (\tilde{h}_1 j_1, \tilde{h}_2 j_2, \tilde{h}_3 j_3), j = (j_1, j_2, j_3), \text{ for } 0 \leq j_q < \tilde{N}_q, q=1,2,3. \quad (1.5)$$

To enforce smoothness of the motion function, $\tilde{h}_q \gg h_q$ and $\tilde{N}_q \gg N_q$ are selected and $c_j(s)$ is some function of time. To make sure the motion grid (1.5) covers the same region as the reconstruction grid (1.1), it is required that:

$$\tilde{h}_q \tilde{N}_q = h_q N_q =: H_q. \quad (1.6)$$

Then $$\vec{\varphi}(s, \vec{x}) = \sum_{i \leq j_q < \tilde{N}_q} \vec{c}_j(s) \tilde{\varphi}_h(\vec{x} - \vec{m}_j). \quad (1.7)$$

For the data points outside the actual data region, the clamped boundary condition is used, i.e., the data point outside the domain has the same value as the closest boundary value.

In accordance with the present invention, the method and associated algorithm solves the motion estimation problem by finding functions $f(s, \vec{x})$ and $\vec{\varphi}(s, \vec{x})$, so that the following equation holds:

$$f(s, \vec{x}) = f_0(\vec{\psi}(s, \vec{x})), \quad (2.1)$$

where $f_0(\vec{x})$ is the volume of the attenuation coefficient at reference time. Introduce a function $\vec{u}(s, \vec{x})$, which is the inverse of $\vec{\varphi}(s, \vec{x})$. More precisely:

$$\vec{\mu}(s, \vec{\psi}(s, \vec{x})) = \vec{x}, \vec{\psi}(s, \vec{\mu}(s, \vec{x})) = \vec{x}. \quad (2.2)$$

Equation:

$$\vec{y} = \vec{\mu}(s, \vec{x}) \quad (2.3)$$

means that the physical point, which was located at $\tilde{x}$ at reference time $s_{ref}$, is located at $\tilde{y}$ at current time $s$. In particular, for a fixed $\vec{x}$, $\vec{u}(s, \vec{x})$ is just the curve describing the motion of the particle due to breathing. Hence, the derivative:

$$\vec{v}(s, \vec{x}) = \partial \vec{\mu}(s, \vec{x})/\partial s \quad (2.4)$$

is simply the velocity of the particle. Replacing $\vec{x}$ with $\vec{u}(s, \vec{x})$ in (2.1) and use (2.2) to find:

$$f(s, \vec{\mu}(s, \vec{x})) = f_0(\vec{x}), \quad (2.5)$$

i.e., the left side of (2.5) is independent of s. Differentiate (2.5) with respect to s and use (2.4) gives:

$$\frac{\partial f(s, \vec{\mu}(s, \vec{x}))}{\partial s} + \nabla f(s, \vec{\mu}(s, \vec{x})) \cdot \vec{v}(s, \vec{x}) = 0. \quad (2.6)$$

Denote $\vec{y} = \vec{u}(s, \vec{x})$. Then, because of (2.2), $\vec{x} = \vec{\psi}(s, \vec{y})$. Using in (2.6) gives:

$$\frac{\partial f(s, \vec{y})}{\partial s} + f(s, \vec{y}) \cdot \vec{v}(s, \vec{\psi}(s, \vec{y})) = 0. \quad (2.7)$$

Denote:

$$\vec{v}*(s, \vec{y}) := \vec{v}(s, \vec{\psi}(s, \vec{y})). \quad (2.8)$$

Then (2.7) simplifies as follows:

$$\frac{\partial f(s, \vec{y})}{\partial s} + \nabla f(s, \vec{y}) \cdot \vec{v}_*(s, \vec{y}) = 0. \quad (2.7)$$

Thus, (2.9) is a necessary condition for a function $f(s, \vec{y})$ to satisfy (2.5).

Following is a more detailed description of the proposed method of the invention.

Let $s_m$, $0 \leq m < M$, be the collection of times corresponding to the measured views, and $L_{mk}$, $0 \leq k < K$, be the collection of lines corresponding to the mth radiation source position. In other words, $L_{mk}$ is the line through the mth source position and the kth detector pixel. It is assumed that the detector consists of K pixels. The measured data are denoted $G_{mk}$.

Finding $f(s, \vec{y})$ and $\vec{v}*(s, \vec{y})$ can be done by minimizing the following functional:

$$\Phi(f, \vec{v}_*) = \frac{1}{2} \sum_{mk} w_{mk} \left[ G_{mk} - \int_{L_{mk}} f(s_m, \vec{x}) d\ell \right]^2 + \quad (2.10)$$

$$\frac{\lambda}{2} \sum_i \int_0^{\Delta S} \left[ \frac{\partial f(s, \vec{x}_i)}{\partial s} + \nabla f(s, \vec{x}_i) \cdot \vec{v}_*(s, \vec{x}_i) \right]^2 ds +$$

(penalty term enforcing smoothness of $f$) +

(penalty term enforcing smoothness of $\vec{v}_*$).

Here $\lambda > 0$ needs to be a large number to enforce the OFC (2.9). In general, volume image is considered as a non-smooth function, while the velocity is considered to be smooth. To match the characteristics of each image, an edge-preserving regularizer for the volume penalty term (hyperbolic potential), and the Tikhonov regularizer for the velocity penalty term are used.

In a particular embodiment, an alternating minimization is used to demonstrate the performance of the proposed method, but other numerical minimization techniques may be applied to find the optimal solution.

In performing the alternating minimization and dynamic parameter selection, let there be $N_p$ discrete phase bins. For computational efficiency, $G_{mk}$ is sorted into a group of subsets $G_p$ so that the pth subset corresponds to the data within the pth phase bin, i.e., $s_p \leq s_m < s_{p+1}$. Let f and v denote phase and velocity volumes unrolled into 1D vectors, respectively. Then (2.10) can be rewritten in a matrix-vector form as follows:

$$\Phi(f,v) = \Phi_L(f) + \lambda \Phi_{f_v}(f,v) + k_f \Phi_{R_f}(f) + k_v \Phi_{R_v}(v), \quad (3.1)$$

where $\Phi_L(f)$ is the data fidelity function, $\Phi_{f_v}(f,v)$ is the OFC penalty, $\Phi_{R_f}(f)$ is the volume regularizer, and $\Phi_{R_v}(v)$ is the velocity regularizer defined as:

$$\Phi_L(f) := \frac{1}{2}(G - Af)^T W(G - Af) \quad (3.2)$$

$$= \frac{1}{2} \sum_p (G_p - A_p f_p)^T W_p (G_p - A_p f_p)$$

-continued $$\Phi_{fv}(f, v) := \frac{1}{2}\left\|Df + \sum_q \text{diag}\{Bv_q\}C_qf\right\|_2^2, \quad (3.3)$$

$$= \frac{1}{2}\sum_p \left\|[Df]_p + \sum_q \text{diag}\{Bv_{p,q}\}C_qf_p\right\|_2^2,$$

$$\Phi_{R_f}(f) := \sum_q \sum_i \phi_R([C_qf]_i, \delta), \quad (3.4)$$

$$= \sum_p \sum_q \sum_i \phi_R([C_qf_q]_i, \delta),$$

$$\Phi_{R_v}(v) := \frac{1}{2}\sum_q \sum_r \|C_r v_q\|_2^2 \quad (3.5)$$

$$= \frac{1}{2}\sum_p \sum_q \sum_r \|C_r v_{p,q}\|_2^2,$$

where a. G is the entire set of measured data, and $G_p$ is the subset of measured data corresponding to the pth phase bin, b. f is the entire set of phase volumes in vector form, and $f_p$ is the pth phase volume in vector form, c. v is the entire set of phase velocity form, and $v_{p,q}$ is the qth axis component of velocity vector $\vec{v}^*$ at pth phase bin in vector form, d. A is the entire projection matrix that projects f onto the data domain corresponding to G, and $A_p$ is the projection matrix that projects $f_p$ onto the data domain corresponding to $G_p$, e. W is the entire set of weighting matrices, and $W_p$ is the weighting matrix corresponding to $G_p$, f. B is the upsampling matrix by cubic B-spline interpolation with the upsampling rate $N_q/\tilde{N}_q$ along the qth axis, g. D is the temporal finite difference matrix along the phase bins with periodic boundary conditions, h. $C_q$ is the spatial finite difference matrix along the qth axis with clamped boundaries. Its dimension is determined by the vector to which it applies, i. diag $\{t\}$ is the diagonal matrix with the elements of vector t on the main diagonal, j. $[t]_i$ is the ith element (scalar, vector, or matrix) along the first dimension of ector or matrix t.

k. $\phi_R(t, \delta)$ is the element-wise hyperbolic potential defined as:

$$\phi_R(t,\delta)=\delta^2(\sqrt{1+(t/\delta)^2}-1), \quad (3.6)$$

and $\delta$ is the shape parameter defining the "edge".

Note that even though every linear operation is expressed in matrix form in (3.1)-(3.5), the actual computation does not store those matrices in memory, but instead calculates each element when needed. Also note that $\Phi_L$, $\Phi_{R_f}$ and $\Phi_{R_v}$ are phase-separable, i.e., computing the pth terms does not require to access data $G_l$ or parameters $f_l$ and $v_l$ for all $l \neq p$, which is preferred for multi-device parallel computing. However, $\Phi_{fv}$ is phase-coupled, and it requires accessing neighboring phases. This data exchange latency can be reduced by computing other phase-separable terms while copying data.

The present invention employs a method of alternating minimization, with respect to volume and velocity. The total cost functional in (3.1) is nonlinear, nonconvex and ill-posed. Minimizing (3.1) with respect to volume and velocity simultaneously often falls into undesirable local minima. The method of alternating minimization, in accordance with the present invention, helps to solve the problem by splitting the problem into two simpler sub-problems and guiding the solution to the desired local minimum.

Figure 2:
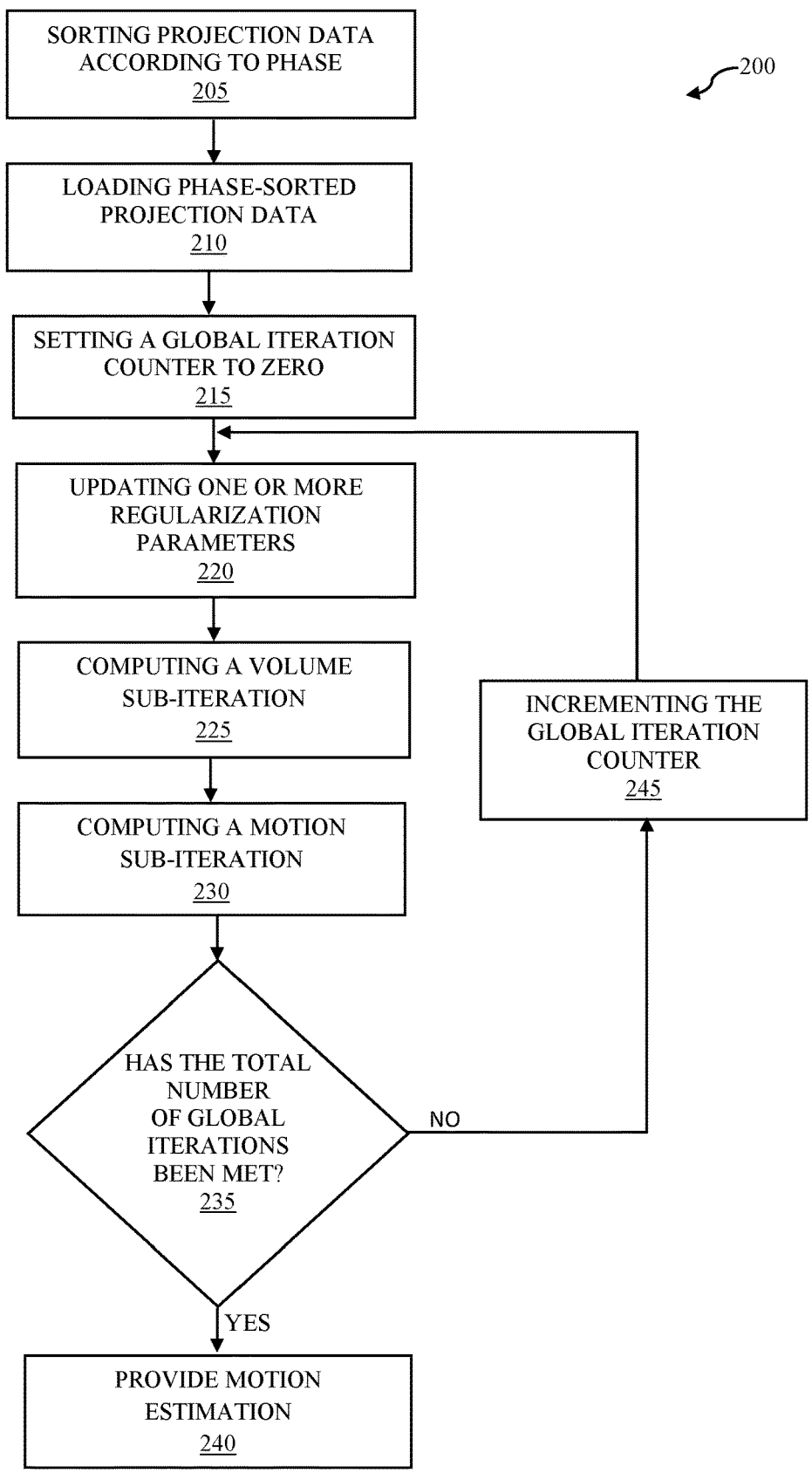
FIG. 2 is a flow diagram illustrating the global iteration process for motion estimation, in accordance with an embodiment of the present invention.
Figure 3:
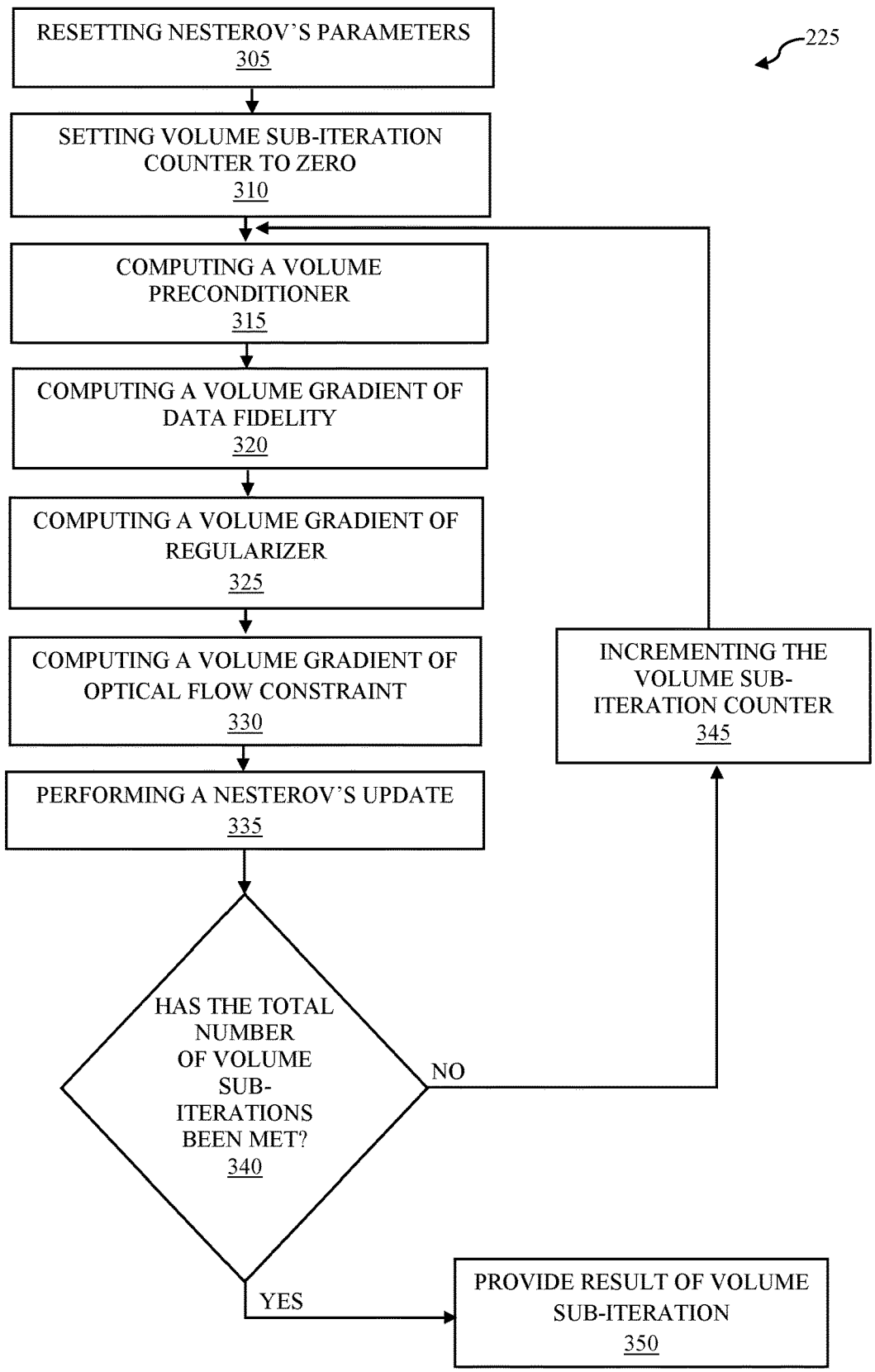
FIG. 3 is a flow diagram illustrating the volume sub-iteration process for motion estimation, in accordance with an embodiment of the present invention.
Figure 4:
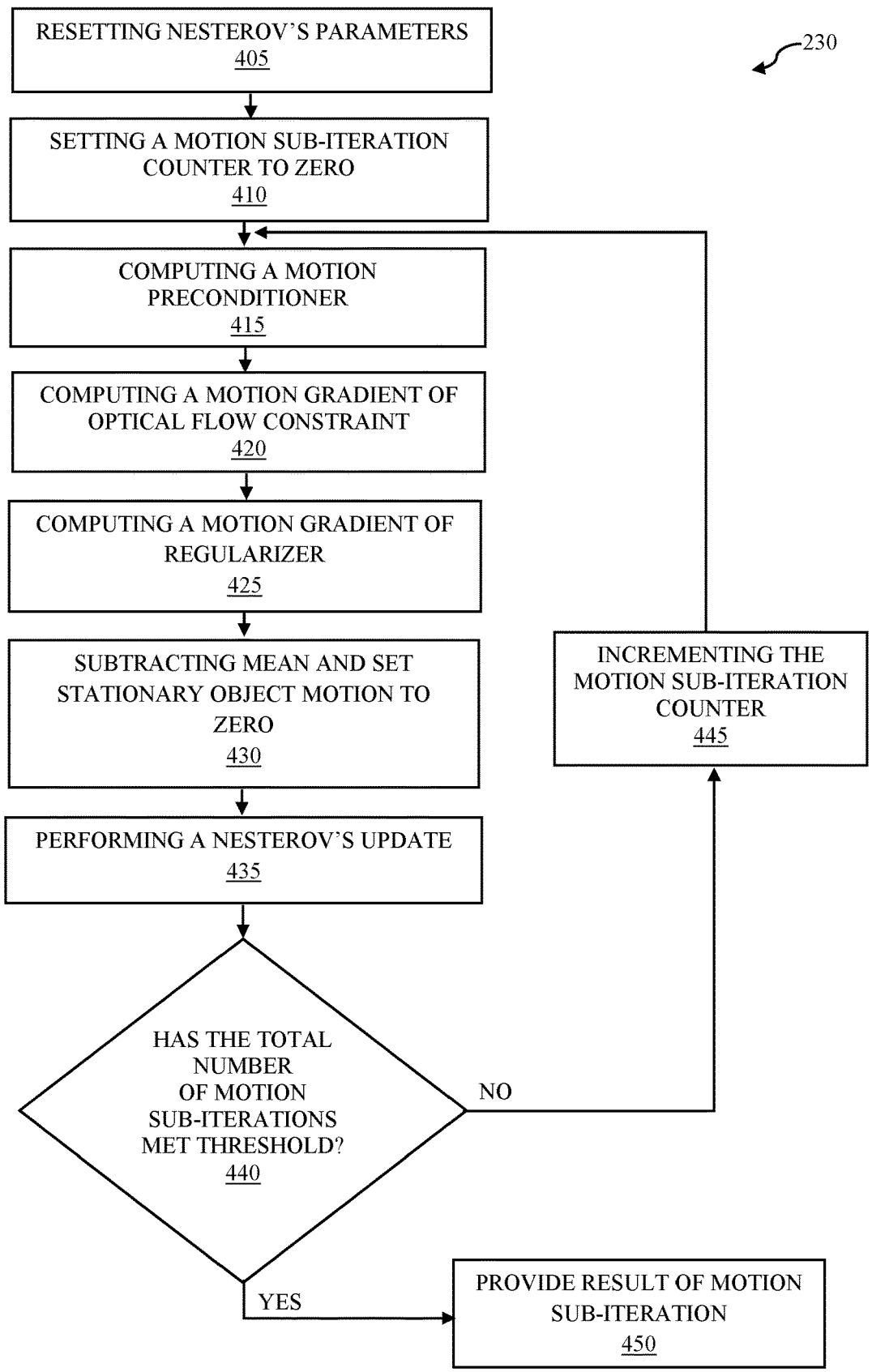
FIG. 4 is a flow diagram illustrating the motion sub-iteration process for motion estimation, in accordance with an embodiment of the present invention.

With the alternating minimization scheme, each global iteration step consists of a set of volume sub-iterations and a set of velocity sub-iterations. In each sub-iteration, the cost functional is minimized with respect to f and with respect to v in an alternating fashion while keeping the other variable fixed. This way, each sub-problem becomes convex, which is easier to solve. Also, parameters of the minimization problem are tuned based on the properties of the currently computed solution or using some other consideration. FIG. 2, FIG. 3 and FIG. 4 are flowcharts illustrating a global iteration, volume sub-iteration and motion sub-iteration, respectively.

The method steps 200 of the present invention for global iteration are illustrated with reference to FIG. 2. Assuming the projection data of the object has been previously collected by a scanner, the method begins by sorting the projection data according to the phase 205. At a next step 210, the phase-sorted projection data is loaded into the data processor, and the global iteration counter is set to zero in the following step 215. The method proceeds by computing one or more regularization parameters at step 220. At step 225, a volume sub-iteration is performed followed by a motion sub-iteration at step 230. The method then checks at step 235 to see if the global iteration counter is equal to a total number of global iteration steps. If the total number of global iteration steps has not yet been reached, at step 245, the iteration counter is incremented and steps 225 and 230 are repeated. The process iteratively repeats until the total number of global iteration steps has been met and the motion has been estimated. The estimated motion can then be used to perform a separate motion compensated reconstruction of the image from the projection data. Alternatively, the set of phase volumes obtained at the end of the last volume sub-iteration can be used by the practitioners.

FIG. 3 further details the volume sub-iteration process 225 of the global iteration process 200 for motion estimation. As shown in FIG. 3, the volume sub-iteration process 225 begins at step 305 by resetting Nesterov's parameters. The method continues at step 310 by setting a volume sub-iteration counter to zero. At step 315, a volume preconditioner is computed. At step 320 a volume gradient of data fidelity is computed and at step 325 a volume gradient of regularizer is computed. The method continues at step 330 by computing a volume gradient of the OFC at then performing a Nesterov update at step 335. At step 340, if the volume sub-iteration counter is not equal to a total number of volume sub-iteration steps, the method continues at step 345 by incrementing the volume sub-iteration counter and iteratively repeating the steps of computing a volume preconditioner 315, computing a volume gradient of data fidelity 320, computing a volume gradient of regularizer 325, computing a volume gradient of the volume-velocity coupling 330 and performing a Nesterov update 335 until the volume sub-iteration counter is determined to be equal to the total number of volume sub-iteration steps at step 340. At step 350, the result of the volume sub-iterations is returned after the total number of volume sub-iteration steps has been met.

FIG. 4 further details the motion sub-iteration process 230 of the global iteration process 200 for motion estimation. As shown in FIG. 4, the motion sub-iteration process 230 begins at step 405 by resetting Nesterov's parameters. The method continues at step 410 by setting a motion sub-iteration counter to zero. At step 415 a velocity preconditioner is computed. A velocity gradient of the OFC is computed at step 420 and a velocity gradient of regularizer is computed at step 425. To remove the false constant motion, the voxel-wise phase mean velocity is subtracted in every motion sub-iteration and the velocity at the boundaries of the ROI (region of interest) is set to zero at step 430. A Nesterov update is then performed at step 435 and if a difference between consecutive sub-iteration values of the functional being minimized is not lower than a specified threshold value, at step 445 the method continues by incrementing the motion sub-iteration counter and iteratively repeating the steps of computing a motion preconditioner 415, computing a velocity gradient of the OFC 420, computing a velocity gradient of regularizer 425, subtracting the mean 430 and performing a Nesterov update 435. The method continues until the difference between consecutive sub-iteration values of the functional being minimized is determined to be lower than the specified threshold value at step 440. At step 450, the result of the motion sub-iteration is returned after the total number of specified threshold has been met.

Starting volume sub-iterations with a large $\lambda$ when the velocity is initialized as zero often results in an underestimation of the motion. In the extreme case, when $\lambda \to \infty$, phase volume images are averaged at the end of the initial set of volume sub-iterations. Once motion information is lost in the phase-volume images due to the averaging effect, it is hard to recover the motion in the following velocity sub-iterations. To appropriately utilize the OFC penalty, a changing $\lambda$ is required. On the other hand, the data sampling rate of the phase subset data $G_p$ is very low compared to the full angle CT, thus strict phase gating methods often create strong sparse data streak artifacts that adversely affect velocity estimation.

To address this problem, the global iteration process illustrated in FIG. 1 is started with a weak OFC coefficient $\lambda$ to avoid motion underestimation and strong volume regularizer $\varkappa_f$ to reduce sparse view-sampling streaks. Then, $\lambda$ is gradually ramped-up and $\varkappa_f$ is simultaneously reduced to restore details. For example, the following values for $\lambda$ and $\varkappa_f$ may be used at each global iteration step $n_g$ using parameters $\lambda_{max}$, $\varkappa_{max}$ and $\varkappa_{min}$:

$$\lambda(n_g) = \min\left(\lambda_{max} \frac{n_g}{N_g - 1}, \lambda_{max}\right), \tag{3.7}$$

$$\kappa_f(n_g) = \max(\kappa_{max} 2^{-n_g}, \kappa_{min}), \tag{3.8}$$

where $N_g$ is the total number of global iteration steps. The estimated velocity is merely an approximation, which may or may not contain errors. To avoid overly-relying on the estimated velocity, $\lambda$ is set to be no greater than $\lambda_{max}$ to limit the maximum volume-velocity constraint strength. Also, $\varkappa_f$ is set to be no less than $\varkappa_{min}$ to maintain the denoising property of the regularizer. $\varkappa_{min}$ needs to be chosen depending on the intensity of noise in the measured data. In another embodiment, the strength of the OFC may change non-monotonically during global iterations, e.g. in an oscillatory way.

In the present invention, a preconditioner and Nesterov's momentum acceleration method are applied to each sub-iteration step to increase the convergence speed. No acceleration of global iterations is applied, due to the risk of overshooting the instability, considering the global functional is not convex.

In the volume-iteration of the present invention, an approximated Newton's method is used with separable quadratic surrogate preconditioner. First, the gradient of the cost functional with respect to the volume parameters is found as:

$$f_p^{(n_g, n_s+1)} = f_p^{(n_g, n_s)} - \hat{H}_{f_p}^{-1} \nabla_{f_p} \Phi(f^{n_g, n_s}, v^{(n_g-1)}), \tag{3.9}$$

where $n_s$ is the sub-iteration step, $v^{(n_g-1)}$ is the result of the velocity sub-iterations in $(n_g-1)$th global iteration step, $\nabla_t$ is the gradient operator with respect to t, and $\hat{H}_t$ is the preconditioner for the update of t. Volume gradient of each component of $\Phi$ is as follows:

$$\nabla_{f_p} \Phi_L(f) = A_p^T W_p (A_p f_p - G_p), \tag{3.10}$$

$$\nabla_{f_p} \Phi_{fv}(f, v) = \left\{ [D^T g]_p + \sum_q C_q^T \mathrm{diag}\{Bv_{p,q}\} g_p \right\} \tag{3.11}$$

$$\nabla_{f_p} \Phi_{R_f}(f) = \sum_p \sum_q C_q^T \dot{\phi}_R(C_q f_p, \delta), \tag{3.12}$$

where g in (3.11) is defined as:

$$g := Df + \sum_q \mathrm{diag}\{Bv_q\} C_q f, \tag{3.13}$$

and $\dot{\phi}_R(t, \delta)$ is the first derivative of $\phi_R$ with respect to t.

To design the preconditioner $\hat{H}_f$ the true Hessian must first be found. Let $H_f$ denote the true Hessian of $\Phi(f, v)$ with respect to f:

$$H_f := \nabla_f^2 \Phi(f, v) = \nabla_f^2 \Phi_L(f) + \lambda \nabla_f^2 \Phi_{fv}(f, v) + \kappa_f \nabla_f^2 \Phi_{R_f}(f), \tag{3.14}$$

$$H_f^L := \nabla_f^2 \Phi_L(f) = A^T W A, \tag{3.15}$$

$$H_f^{fv} := \nabla_f^2 \Phi_{fv}(f, v) = D^T D + D^T \sum_q \mathrm{diag}\{Bv_q\} C_q + \sum_q C_q^T \mathrm{diag}\{Bv_q\} D + \sum_q C_q^T \mathrm{diag}\{Bv_q\}^2 C_q, \tag{3.16}$$

$$H_f^{R_f} := \nabla_f^2 \Phi_{R_f}(f) = \sum_q C_q^T \mathrm{diag}\{\ddot{\phi}_R(C_q f, \delta)\} C_q, \tag{3.17}$$

$H_f$ is not phase-separable, and the size of $H_f$ is very large. Inverting $H_f$ is time-consuming, so it is desirable to have a separable (diagonal) preconditioner for each phase bin volume $\hat{H}_{f_p}$ such that $\hat{H}_{f_p} \succcurlyeq H_{f_p}$ to avoid large matrix inversion. The same applies to other Hessians as well:

$$\hat{H}_{f_p} := \hat{H}_{f_p}^L + \lambda \hat{H}_{f_p}^{fv} + k_f \hat{H}_{f_p}^{R_f}. \tag{3.18}$$

Beginning with the following estimates:

$$H_{f_p}^L \preceq \mathrm{diag}\{A_p^T W_p A_p 1_N\}, \tag{3.19}$$

-continued $$H_{f_p}^{f_v} \preceq \rho(D)^2 I_N + 2\rho(D)\rho(C_q)\text{diag}\left\{Bvec\left\{\sum_q \max_{i \in \mathcal{P}_p}|v_{i,q,j}|\right\}\right\} + \quad (3.20)$$

$$\rho(C_q)^2 \text{diag}\left\{Bvec\left\{\sum_q \max_{i \in \mathcal{P}_p}(v_{i,q,j})^2\right\}\right\} =$$

$$4I_N + 8\text{diag}\left\{Bvec\left\{\sum_q \max_{i \in \mathcal{P}_p}|v_{i,q,j}|\right\}\right\} +$$

$$4\text{diag}\left\{Bvec\left\{\sum_q \max_{i \in \mathcal{P}_p}(v_{i,q,j})^2\right\}\right\},$$

$$H_{f_p}^{R_f} \preceq 3\rho(C_q)^2 I_N = 12 I_N, \quad (3.21)$$

where $\rho(T)$ is the spectral radius of a matrix T, $vec(t_1)$ is the unrolled 1D vector of data t in 3D coordinate I, $\mathcal{P}_p$ is the set of adjacent phase bins $\mathcal{P}_p = \{l | p-1 \le l \le p+1\}$, $1_N$ is the all-ones vector of size $N = \Pi_q N_q$, and $I_N$ is the identity matrix of size N×N. Storing the preconditioner (3.19) requires a large memory space. Assuming the angular sampling frequency of the phase-gated data $G_p$ is approximately the same for every phase bin, (3.19) can be approximated using the averaged preconditioner:

$$\hat{H}_{f_p}^L =: \frac{2M_p}{M}\text{diag}\left\{\sum_l A_l^T W_l A_l 1_N\right\}, \quad (3.22)$$

where $M_p$ is the total number of projection data in the pth phase bin. The factor 2 in the numerator is the safety factor in case the angular sampling frequency of each phase bin projection data is not similar to each other.

Also, storing the preconditioner (3.20) requires a considerable amount of memory. To reduce memory storage, (3.20) can be further simplified using a single maximum value:

$$\hat{H}_{f_p}^{f_v} =: \left(4 + 24\max_{l,q,j}|v_{l,q,j}| + 12\max_{l,q,j}(v_{l,q,j})^2\right)I_N. \quad (3.23)$$

Finally, for the volume regularization term is used:

$$\hat{H}_{f_p}^{R_f} =: 12 I_N. \quad (3.24)$$

The volume gradient descent update in (3.9) with the final preconditioner (3.18) is only linearly converging. To speed-up the convergence, Nesterov's momentum acceleration method is applied. If each phase-gated data has significantly biased angular sampling, (3.22) might lead to instability. To avoid the instability, Nesterov acceleration is reset whenever the cost functional value increases during the iteration.

As previously described, in addition to the volume sub-iteration, the present invention also employs a velocity sub-iteration. Similar to the volume sub-iteration step, an approximated Newton's method is used with a separable quadratic surrogate preconditioner. The velocity gradient is obtained as follows:

$$v_{p,q}^{(n_g, \bar{n}_s+1)} = v_{p,q}^{(n_g, \bar{n}_s)} - \hat{H}_{v_{p,q}}^{-1} \nabla_{v_{p,q}} \Phi(f^{(n_g-1)}, v^{(n_g, \bar{n}_s)}), \quad (3.25)$$

$$\nabla_{v_{p,q}} \Phi_{f_v}(f,v) = B^T(\text{diag}\{C_q f_p\} g_p), \quad (3.26)$$

$$\nabla_{v_{p,q}} \Phi_{R_v}(v) = C_q^T C_q v_{p,q}, \quad (3.27)$$

where $f^{(n_g-1)}$ is the result of the volume sub-iterations in $(n_g-1)$th global iteration step. Similar to (3.23) and (3.24), the separable preconditioner for the volume update can be obtained as follows:

$$\hat{H}_{v_{p,q}} =: \lambda \hat{H}_{v_{p,q}}^{f_v} + \kappa_v \hat{H}_{v_{p,q}}^{R_v}, \quad (3.28)$$

$$\hat{H}_{v_{p,q}}^{f_v} =: B^T \text{diag}\left\{\sum_r |C_r f_p|_e\right\}|C_q f_p|_e, \quad (3.29)$$

$$\hat{H}_{v_{p,q}}^{R_v} =: 12 I_{\bar{N}}, \quad (3.30)$$

where $|t|_e$ is the element-wise absolute value operator. Nesterov's momentum acceleration is also applied to the velocity gradient update to speed-up the convergence.

While volume sub-iterations do not need to be fully converged at each global iteration step, as details can be restored at later global iterations, stopping velocity sub-iterations while the cost functional is not fully converged typically leads to a loss of small, detailed motions. To avoid this condition, each set of velocity sub-iterations is run until the difference between the values of the cost functional at consecutive sub-iterations is lower than a specified threshold. In contrast, each set of volume sub-iterations is run for a fixed number of iterations.

After a set of motion sub-iterations converges for the first time, motion sub-iterations of the subsequent global iteration steps converge much faster. On the other hand, volume sub-iterations slow down as the global iteration number increases. This is due to the competition between the data fidelity and OFC terms. The latter becomes stronger as the global iterations progress. To accommodate the slower rate of convergence of the volume sub-iterations, the total number of volume sub-iterations may be increased per set by 100 every global iteration.

Motion estimation in the region where there is no object is vulnerable to instability. Although the regularizer prevents the unstable, behavior, the estimated velocity often shows false constant motion. To remove the false constant motion, the voxel-wise phase mean velocity is subtracted in every motion sub-iteration. This mean subtraction process does not improve image quality significantly as most of the false constant motion happens in empty regions, but it helps the convergence speed and stability of the motion iterations as the maximum velocity is reduced. Also, the velocity at the boundaries of the ROI (region of interest) is set to zero, because nothing is moving there. Going further, if the location of a stationary object, such as a patient couch, is known, velocity can be set to zero inside those regions.

In an additional embodiment, motion estimation can be based upon a parameterized cyclic deformation model. In this embodiment, the OFC approach is reformulated using the deformation function instead of the MVFs. Using (2.5), one way to incorporate the OFC (which is an alternative to Equation (2.9)) is via:

$$\Phi_{f\mu}(f, \vec{\mu}) = \sum_i \sum_p \left| f(s_p, \vec{\mu}(s_p), \vec{x}_i)) - \frac{1}{M}\sum_{p'} f(s_{p'}, \vec{\mu}(s_{p'}), \vec{x}_i)) \right|^m, \quad (4.1)$$

for some m>0. The choices m=1, 2 are popular ones. Another option is:

$$\Phi_{f\mu}(f,\vec{\mu}) = \sum_i \sum_p |f(s_{p+1}, \vec{\mu}(s_{p+1}, \vec{x}_i)) - f(s_p, \vec{\mu}(s_p, \vec{x}_i))|^m. \quad (4.2)$$

Eq. (2.9) describes the OFC in the differential form, and Eqs. (4.1), (4.2) describe the OFC in integral form.

The functional $\Phi_{f\mu}$ should replace $\Phi_{fv}$ in (2.10). Similarly, the regularization of the velocity term should be replaced by the regularization of the motion function $\vec{\mu}$. The resulting functional can also be minimized using the alternating minimization approach. It is still linear with respect to f(s, $\vec{x}$). Even though the functional is non-linear with respect to $\vec{\mu}$(s, $\vec{x}$), iterations with respect to $\vec{\mu}$(s, $\vec{x}$) are fairly easy and not time consuming, since they do not require access to raw data.

Using the deformation-based approach, several advantages may be realized:

1) It can be enforced that each particle moves periodically along a line segment (or, along an elliptical path).
2) Such a description will have fewer parameters for compute, which will make the overall ME/MC (motion estimation/motion compensation) problem more stable.
3) Since the proposed description has fewer parameters, some of these parameters can be allowed to slowly change during the scan to account for irregular breathing.
4) Initially, for improved stability, it can be assumed that the phase of each voxel is the same as the phase observed by the tracking device on the patient's chest. At later iterations, this requirement can be relaxed.
5) Rigid body constraints can be enforced inside high-attenuating regions, such as bones. This can be achieved for example by thresholding the reconstruction volume (starting after sufficiently many global iterations) and enforcing that neighboring voxels within highly attenuating regions have the same motion function and by adjusting the strength parameter of motion regularization separately at each data point of motion grid based on the corresponding volume to softly encourage the rigid motion at highly attenuating regions. Generally, it is not advisable to add more constraints to the optimization problem, because it may dilute the effect of the data fidelity term. Here, such a problem does not arise, because volume iterations will not see these additional constraints. They will be formulated only in terms of the bone mask (in approach (a)) or in terms of the solution $f^{(n_g)}$ at some fixed intermediate iteration $n_g$ (in approach (b)).
6) Use the data fidelity weight $w_{mk}$ to account for the reliability of the estimated phase of each measure view.
7) Generally, it is easier to incorporate any other physical constraint.
8) Having easy access to the phase information (as part of the deformation function), one can reduce the progressive wave that causes false circular motion by using appropriate regularization, and leave only the stationary wave that is more physical. Similarly to item (5), the requirement that nearby points have approximately the same phase is invisible to volume iterations.
9) An advantage of (4.1) and (4.2) over (2.10) is that the former do not use the derivatives of f, hence the requirements on the smoothness of f are relaxed. This may lead to improved spatial and temporal resolution of the method.
10) The proposed method automatically guarantees the cyclical motion requirement in the reconstruction.
11) The proposed method does not require computing the inverse of the motion $\vec{\psi} = \vec{\mu}^{-1}$ during iterations.

In an exemplary embodiment, by adopting the second option (4.2) with m=2 multiplied by the conventional constant ½, we get the OFC constraint $$\Phi_{f\mu}(f,\vec{\mu}) = \sum_i \sum_p |f(s_{p+1}, \vec{\mu}(s_{p+1}, \vec{x}_i)) - f(s_p, \vec{\mu}(s_p, \vec{x}_i))|^2. \quad (4.3)$$

The motion model is also chosen as follows, so that each voxel moves along a linear path:

$$\vec{\mu}(s,\vec{x}) = \vec{x} + \left[\cos\left(2\pi \frac{s - \bar{s}(\vec{x})}{\Delta S}\right) - \cos\left(2\pi \frac{\bar{s}(\vec{x})}{\Delta S}\right)\right]\vec{u}(\vec{x}), \quad (4.4)$$

where amplitude $\vec{u}(\vec{x})$ and phase $\vec{s}(\vec{x})$ are given by $$\vec{u}(\vec{x}) = \sum_j \vec{u}_j \varphi(\vec{x} - \vec{m}_j), \quad (4.5)$$

$$\bar{s}(\vec{x}) = \sum_k \bar{s}_k \check{\varphi}(\vec{x} - \vec{n}_k). \quad (4.6)$$

Note that the grids $\vec{x}_i$, $\vec{m}_j$, and $\vec{n}_k$ do not have to be the same, as well as the interpolation functions $\varphi(\cdot)$, $\hat{\varphi}(\cdot)$ and $\check{\varphi}(\cdot)$ do not have to be the same. In general, $\vec{u}$ is smooth, and $\bar{s}$ is even smoother. Thus, a sparse grid can be used with a smooth interpolation function for $\vec{u}$, and even more sparse grid and a smoother interpolation function for $\bar{s}$.

After replacing (3.3) with (4.3) and adding regularization terms for the motion parameters u and $\bar{s}$, the total functional is as follows:

$$\Phi(f,u,\bar{s}) = \Phi_L(f) + \lambda \Phi_{f\mu}(f,u,\bar{s}) + k_f \Phi_{R_f}(f,\delta) + k_u \Phi_{R_u}(u) + k_{\bar{s}} \Phi_R \bar{s}(\bar{s}), \quad (4.7)$$

For $\Phi_{R_u}$ and $\Phi_{R_{\bar{s}}}$, the Tikhonov regularization is used, analogously to $\Phi_{R_v}$ in the previous section.

As in the previous section, an approximated Newton's method with separable surrogate function is used. Here, only the gradient descent part (computation of the gradient and Hessian) of the new motion model is described. All the other terms, such as data fidelity and volume regularization terms, are the same as in the previously described method.

Hereinafter, the following shorthand notations are used for brevity:

$$\vec{\mu}_{p,i} = \vec{\mu}(s_p, \vec{x}_i),$$

$$\mu_{p,i,q} = \mu_q(s_p, \vec{x}_i),$$

$$u_{(i),q} = u_q(\vec{x}_i),$$

$$\bar{s}_{(i)} = \bar{s}(\vec{x}_i),$$

$$\mathcal{F}_{p,1} = f(s_p, \vec{\mu}_{p,1}).$$

In the motion sub-iteration step, the gradient of $\Phi_{f_\mu}$ with respect to the motion vector parameter u is obtained as follows:

$$\frac{\partial \Phi_{f_\mu}}{\partial u_{j,q}} = \sum_{i \in \check{I}(j)} \sum_p \left[ (\mathcal{F}_{p+1,i} - \mathcal{F}_{p,1}) \left( \frac{\partial \mathcal{F}_{p+1,i}}{\partial \mu_{p+1,i,q}} \frac{\partial \mu_{p+1,i,q}}{\partial u_{j,q}} - \frac{\partial \mathcal{F}_{p,i}}{\partial \mu_{p,i,q}} \frac{\partial \mu_{p,i,q}}{\partial u_{j,q}} \right) \right], \quad (4.8)$$

where $\check{I}(j) = \{i | \hat{\varphi}(\vec{x}_i - \vec{m}_j) \neq 0\}$, and $$\frac{\partial \mu_{p,i,q}}{\partial \bar{s}_k} = \frac{2\pi}{\Delta S} \left( \sin\left(2\pi \frac{s_p - \bar{s}_{(i)}}{\Delta S}\right) + \sin\left(2\pi \frac{\bar{s}_{(i)}}{\Delta S}\right) \right) u_{(i),q} \cdot \check{\varphi}(\vec{x}_i - \vec{n}_k). \quad (4.9)$$

With bilinear interpolation, the analytic form of $$\frac{\partial \mathcal{F}_{p+1,i}}{\partial \mu_{p+1,i,q}}$$

cannot be computed, as $\varphi$ is not differentiable. Instead, we compute it numerically by applying the central difference first, then find the value at $\mu_{p+1,i,q}$. Similarly, the gradient of $\Phi_{f_\mu}$ with respect to the motion phase parameters is obtained as follows:

$$\frac{\partial \Phi_{f_\mu}}{\partial \bar{s}_k} = \sum_{i \in \check{I}(k)} \sum_p \left[ (\mathcal{F}_{p+1,i} - \mathcal{F}_{p,i}) \cdot \right. \quad (4.10)$$

$$\left. \sum_q \left( \frac{\partial \mathcal{F}_{p+1,i}}{\partial \mu_{p+1,i,q}} \frac{\partial \mu_{p+1,i,q}}{\partial \bar{s}_k} - \frac{\partial \mathcal{F}_{p,i}}{\partial \mu_{p,i,q}} \frac{\partial \mu_{p,i,q}}{\partial \bar{s}_k} \right) \right],$$

where $\check{I}(k) = \{i | \hat{\varphi}(\vec{x}_i - \vec{m}_k) \neq 0\}$, and $$\frac{\partial \mu_{p,i,q}}{\partial \bar{s}_k} = \frac{2\pi}{\Delta S} \left( \sin\left(2\pi \frac{s_p - \bar{s}_{(i)}}{\Delta S}\right) + \sin\left(2\pi \frac{\bar{s}_{(i)}}{\Delta S}\right) \right) u_{(i),q} \cdot \check{\varphi}(\vec{x}_i - \vec{n}_k). \quad (4.11)$$

The Hessian of $\Phi_{f_\mu}$ is obtained as follows:

$$\frac{\partial^2 \Phi_{f_\mu}}{\partial u_{j,q} \partial u_{j',q'}} = \quad (4.12)$$

$$\sum_{i \in \check{I}(j) \cap \check{I}(j')} \sum_p \left[ \left( \frac{\partial \mathcal{F}_{p+1,i}}{\partial \mu_{p+1,i,q}} \frac{\partial \mu_{p+1,i,q}}{\partial u_{j,q}} - \frac{\partial \mathcal{F}_{p,i}}{\partial \mu_{p,i,q}} \frac{\partial \mu_{p,i,q}}{\partial u_{j,q}} \right) \cdot \right.$$

$$\left( \frac{\partial \mathcal{F}_{p+1,i}}{\partial \mu_{p+1,i,q'}} \frac{\partial \mu_{p+1,i,q'}}{\partial u_{j',q'}} - \frac{\partial \mathcal{F}_{p,i}}{\partial \mu_{p,i,q'}} \frac{\partial \mu_{p,i,q'}}{\partial u_{j',q'}} \right) +$$

$$(\mathcal{F}_{p+1,i} - \mathcal{F}_{p,i}) \cdot \left( \frac{\partial^2 \mathcal{F}_{p+1,i}}{\partial \mu_{p+1,i,q} \partial \mu_{p+1,i,q'}} \frac{\partial \mu_{p+1,i,q}}{\partial u_{j,q}} \frac{\partial \mu_{p+1,i,q'}}{\partial u_{j',q'}} - \right.$$

$$\left. \left. \frac{\partial^2 \mathcal{F}_{p,i}}{\partial \mu_{p,i,q} \partial \mu_{p,i,q'}} \frac{\partial \mu_{p,i,q}}{\partial u_{j,q}} \frac{\partial \mu_{p,i,q'}}{\partial u_{j',q'}} \right) \right].$$

$$\frac{\partial^2 \Phi_{f_\mu}}{\partial \bar{s}_k \partial \bar{s}_{k'}} = \quad (4.13)$$

$$\sum_{i \in \check{I}(k) \cap \check{I}(k')} \sum_p \left[ \left( \sum_q \frac{\partial \mathcal{F}_{p+1,i}}{\partial \mu_{p+1,i,q}} \frac{\partial \mu_{p+1,i,q}}{\partial \bar{s}_k} - \frac{\partial \mathcal{F}_{p,i}}{\partial \mu_{p,i,q}} \frac{\partial \mu_{p,i,q}}{\partial \bar{s}_k} \right) \cdot \right.$$

$$\left( \sum_q \frac{\partial \mathcal{F}_{p+1,i}}{\partial \mu_{p+1,i,q}} \frac{\partial \mu_{p+1,i,q}}{\partial \bar{s}_{k'}} - \frac{\partial \mathcal{F}_{p,i}}{\partial \mu_{p,i,q}} \frac{\partial \mu_{p,i,q}}{\partial \bar{s}_{k'}} \right) +$$

$$(\mathcal{F}_{p+1,i} - \mathcal{F}_{p,i}) \cdot \left( \sum_{q'} \left( \frac{\partial^2 \mathcal{F}_{p+1,i}}{\partial \mu_{p+1,i,q} \partial \mu_{p+1,i,q'}} \frac{\partial \mu_{p+1,i,q}}{\partial \bar{s}_k} \right. \right.$$

$$\left. \frac{\partial \mu_{p+1,i,q'}}{\partial \bar{s}_{k'}} - \frac{\partial^2 \mathcal{F}_{p,i}}{\partial \mu_{p,i,q} \partial \mu_{p,i,q'}} \frac{\partial \mu_{p,i,q}}{\partial \bar{s}_k} \frac{\partial \mu_{p,i,q'}}{\partial \bar{s}_{k'}} \right) +$$

$$\left. \left. \frac{\partial \mathcal{F}_{p+1,i}}{\partial \mu_{p+1,i,q}} \frac{\partial^2 \mu_{p+1,i,q}}{\partial \bar{s}_k \partial \bar{s}_{k'}} - \frac{\partial \mathcal{F}_{p,i}}{\partial \mu_{p,i,q}} \frac{\partial^2 \mu_{p,i,q}}{\partial \bar{s}_k \partial \bar{s}_{k'}} \right) \right].$$

$$\frac{\partial^2 \Phi_{f_\mu}}{\partial u_{j,q} \partial \bar{s}_k} = \sum_{i \in \check{I}(j) \cap \check{I}(k)} \sum_p \left[ \left( \frac{\partial \mathcal{F}_{p+1,i}}{\partial \mu_{p+1,i,q}} \frac{\partial \mu_{p+1,i,q}}{\partial u_{j,q}} - \frac{\partial \mathcal{F}_{p,i}}{\partial \mu_{p,i,q}} \frac{\partial \mu_{p,i,q}}{\partial u_{j,q}} \right) \cdot \right. \quad (4.14)$$

$$\sum_{q'} \left( \frac{\partial \mathcal{F}_{p+1,i}}{\partial \mu_{p+1,i,q'}} \frac{\partial \mu_{p+1,i,q'}}{\partial \bar{s}_k} - \frac{\partial \mathcal{F}_{p,i}}{\partial \mu_{p,i,q'}} \frac{\partial \mu_{p,i,q'}}{\partial \bar{s}_k} \right) +$$

$$(\mathcal{F}_{p+1,i} - \mathcal{F}_{p,i}) \cdot \left( \sum_{q'} \left( \frac{\partial^2 \mathcal{F}_{p+1,i}}{\partial \mu_{p+1,i,q} \partial \mu_{p+1,i,q'}} \frac{\partial \mu_{p+1,i,q}}{\partial u_{j,q}} \right. \right.$$

$$\left. \frac{\partial \mu_{p+1,i,q'}}{\partial \bar{s}_k} - \frac{\partial^2 \mathcal{F}_{p,i}}{\partial \mu_{p,i,q} \partial \mu_{p,i,q'}} \frac{\partial \mu_{p,i,q}}{\partial u_{j,q}} \frac{\partial \mu_{p,i,q'}}{\partial \bar{s}_k} \right) +$$

$$\left. \left. \frac{\partial \mathcal{F}_{p+1,i}}{\partial \mu_{p+1,i,q}} \frac{\partial^2 \mu_{p+1,i,q}}{\partial u_{j,q} \partial \bar{s}_k} - \frac{\partial \mathcal{F}_{p,i}}{\partial \mu_{p,i,q}} \frac{\partial^2 \mu_{p,i,q}}{\partial u_{j,q} \partial \bar{s}_k} \right) \right].$$

Elements of the Hessian matrix (4.12)-(4.14) are not pixel-independent. One can create a diagonal upper bound matrix (surrogate function) by summing the absolute values of all the coupled terms.

In the volume sub-iteration of the new method, the gradient of $\Phi_{f_\mu}$ with respect to the volume parameter f is obtained as follows:

$$\frac{\partial \Phi_{f_\mu}}{\partial f_{p,i}} = \sum_{t \in T(p,i)} (-\mathcal{F}_{p+1,t} + 2\mathcal{F}_{p,t} - \mathcal{F}_{p-1,t}) \frac{\partial \mathcal{F}_{p,t}}{\partial f_{p,i}}, \quad (4.15)$$

where $T(p, i) = \{t | \varphi(\vec{\mu}_{p,t} - \vec{x}_i) \neq 0\}$, and $$\frac{\partial \mathcal{F}_{p,t}}{\partial f_{p,i}} = \varphi(\vec{\mu}_{p,t} - \vec{x}_i). \quad (4.16)$$

The Hessian of $\Phi_{f_\mu}$ with respect to the volume parameter f is obtained as follows:

$$\frac{\partial^2 \Phi_{f_\mu}}{\partial f_{p,i} \partial f_{p',i'}} = \quad (4.17)$$

-continued $$\begin{cases} \sum_{t \in T(p,i) \cap T(p,i')} 2 \frac{\partial \mathcal{F}_{p,t}}{\partial f_{p,i}} \frac{\partial \mathcal{F}_{p,t}}{\partial f_{p,i'}} & \text{if } p' = p \\ \sum_{t \in T(p,i) \cap T(p',i')} -\frac{\partial \mathcal{F}_{p,t}}{\partial f_{p,i}} \frac{\partial \mathcal{F}_{p',t}}{\partial f_{p',i'}} & \text{if } p' = p-1 \text{ or } p+1 \\ 0 & \text{otherwise} \end{cases}$$

To find the separable surrogate function, the following interpolation properties can be used:

$$0 \le \frac{\partial \mathcal{F}_{p,t}}{\partial f_{p,i}} \le 1 \ \forall t, \quad (4.18)$$

$$\sum_{i \in I(p,t)} \frac{\partial \mathcal{F}_{p,t}}{\partial f_{p,i}} = 1 \ \forall t. \quad (4.19)$$

A diagonal upper bound of the Hessian can be found using the interpolation properties (4.18) and (4.19) as follows:

$$\left[ \frac{\partial^2 \Phi_{f_\mu}}{\partial f_{p,i} \partial f_{p',i'}} \right]_{(p \times i, p' \times i')} \preceq \text{diag} \left\{ \sum_p \sum_{p'} \sum_{i'} \left| \frac{\partial^2 \Phi_{f_\mu}}{\partial f_{p,i} \partial f_{p',i'}} \right| \right\} \quad (4.20)$$

$$= \text{diag} \left\{ 4 \sum_t \frac{\partial \mathcal{F}_{p,t}}{\partial f_{p,i}} \right\}.$$

Note that not all interpolators satisfy the non-negativity property (4.18). One example of such interpolator is the high order polynomial interpolator. The Hessian with interpolators that do not satisfy (4.18) may not be diagonalized using (4.20).

For massively parallel computing, there are two options to compute (4.15) and (4.20):

a. Assign threads along t and loop over all i ∈I(p,t), where $$I(p,t) = \{i | \varphi(\vec{\mu}_{p,t} - \vec{x}_i) \ne 0\},$$

b. Assign threads along i and loop over all t ∈T(p,i).

Finding I(p,t) for each t is easier than finding T(p,i) for each i, because $\vec{\mu}_{p,t}$ is fixed for each thread. On the other hand, approach (b) requires searching along t to find all $\vec{\mu}_{p,t}$ such that t ∈T(p,i). Further more, the size of the support of φ is known prior to computation and in general small, so each t-th thread only needs to access a few $f_{p,i}$s.

However, approach (a) can cause so called, "race condition" as different threads need to read and update the same i location simultaneously. Fortunately, this race condition can be avoided by using atomic operations in CUDA, with some sacrifice of the parallelism. Even better, the race condition does not happen very often when the bilinear interpolation is used as the size of the support is fairly small. Therefore, approach (a) has been chosen to compute (4.15) with bilinear interpolation.

While in the previously described embodiment, the strength of the OFC λ was monotonically increased along the global iterations, it was found that this caused the motion to be consistently underestimated. As such, in this embodiment, instead of a monotonic increase, the OFC strength is changed to oscillate throughout the global iterations with the period of two iterations, i.e. λ=1 for odd iterations, and λ=150 for even iterations.

Odd iterations add more details to the volumes and estimate the motion based on the added details, and even iterations impose the motion on the volumes more strictly. This way, global iterations can keep updating the motion even when the motion is underestimated in earlier iterations.

Figure 5A:
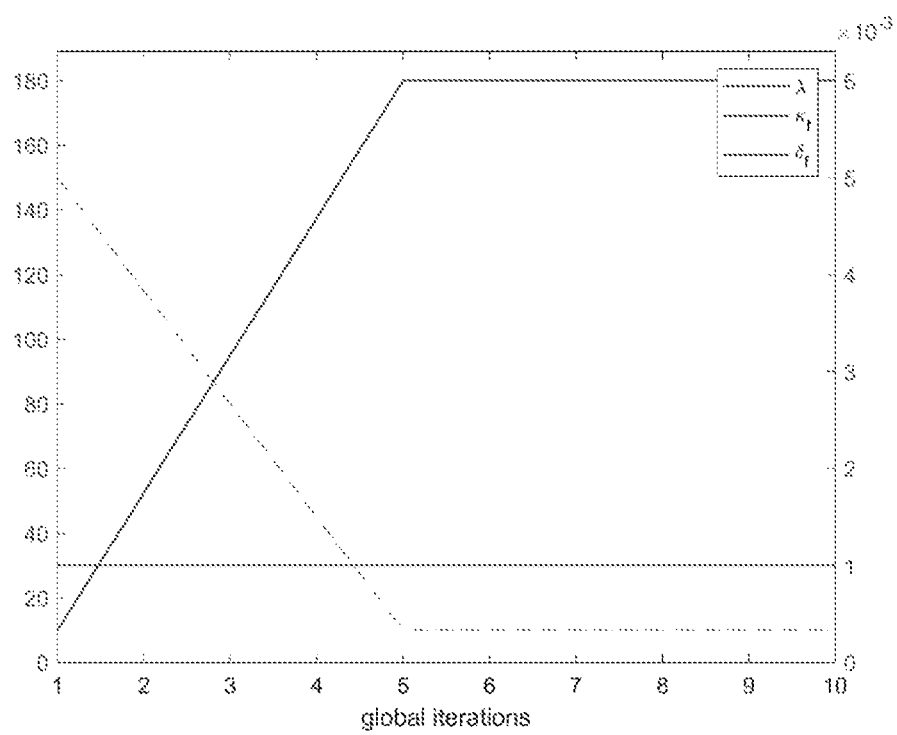
FIG. 5A is a graphical illustration of monotonically incrementing the parameters along the global iterations, in accordance with an embodiment of the present invention.
Figure 5B:
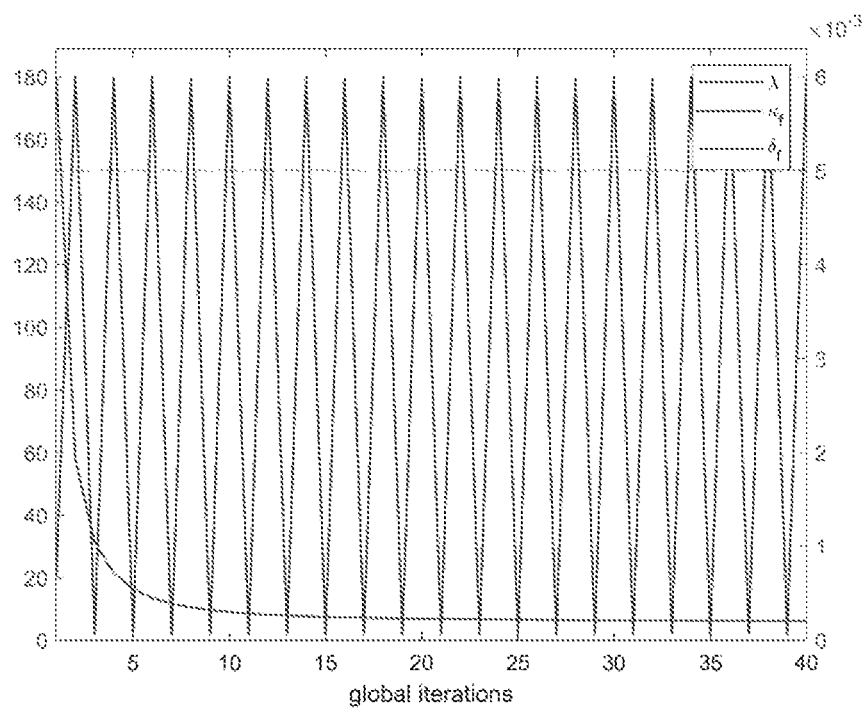
FIG. 5B is a graphical illustration of non-monotonically incrementing the parameters along the global iterations, in accordance with an embodiment of the present invention.

Additionally, in this embodiment, instead of decreasing the volume regularization strength parameter $\varkappa_f$, the volume regularization shape parameter $\delta_f$ is decreased, thereby providing two effects, reduction of regularization strength and transition from Tikhonov type regularization to TV-like regularization as the iterations continue. FIG. 5A illustrates the assigned values of λ, $\varkappa_f$ and $\delta_f$ for each global iteration step in the previously described embodiment, wherein the parameters are increased monotonically. FIG. 5B illustrates the assigned values of λ, $\varkappa_f$ and $\delta_f$ for each global iteration step in the currently described embodiment, wherein the parameters are increased non-monotonically.

While the results for both discrete and continuous motion data are promising, the estimated motion in the continuous case creates slight errors at the boundary. The reason is that even if the reconstructed motion matches the average motion within each phase bin, some projections exceed the deformation range of the estimated motion. As a result, the motion is slightly underestimated and the projections outside the estimate motion create slight streak artifacts in the air account the body being imaged.

The results show that when there is inconsistency of motion within projection data in each phase bin, more studies may be required to achieve the best result. The results also show that artifacts due to replacing continuous motion with discrete motion in simulated experiments are likely negligible compared with artifacts due to significant imperfections in real data, such as breathing motion is not periodic, imperfect binning of data, etc.

Additionally, while the exemplary method and associated algorithm work will with simulated data when there is no residual motion and no noise, applying the same algorithm to clinical data may lead to undesirable speckle artifacts. While the OFC encourages incompressibility, if the volume is indeed incompressible, the data density on the volume grid should be unchanged in every phase. However, the estimated volume usually shows some compressibility (whether it is real or not), and the data density at the expanding region becomes sparse, causing the OFC to be applied unevenly. Consequently, the OFC fails to regularize the expanding or compressing regions properly, resulting in speckle artifacts when the data are noisy and not perfectly matching.

To address these speckle artifacts, MVFs between pairs of consecutive phase volumes on a regular grid are estimated from the motion function $\vec{\mu}(s_p, \vec{x}_i)$ as follows:

$$\vec{V}_p = \underset{\vec{v}}{\arg\min} \frac{1}{2} \sum_i \left| \vec{v}(\vec{\mu}(s_p, \vec{x}_i)) - (\vec{\mu}(s_{p+1}, \vec{x}_i) - \vec{\mu}(s_p, \vec{x}_i)) \right|^2 \quad (5.1)$$

Then the estimated regular grid MVFs is used to impose the OFC in an even fashion (the magnitudes of MVFs are small, so with one grid being regular, its image at the next phase volume is close to a regular grid as well):

$$\Phi_{f_\mu}(f, \vec{\mu}) = \frac{1}{2} \sum_i \sum_p \left| f(s_{p+1}, \vec{x}_i + \vec{V}_p(\vec{x}_i)) - f(s_p, \vec{x}_i) \right|^2. \quad (5.2)$$

In the original OFC, pairs of consecutive phase volumes are compared using a grid, that was regular in the reference phase. This grid is far from regular after deformation:

$$\Phi_{f_\mu}(f, \vec{\mu}) = \frac{1}{2} \sum_i \sum_p \left| f(s_{p+1}, \vec{\mu}(s_{p+1}, \vec{x}_i)) - f(s_p, \vec{\mu}(s_p, \vec{x}_i)) \right|^2. \quad (5.3)$$

Accordingly, is this embodiment, the OFC is modified to use MVFs on a regular grid to remove the speckle artifacts.

The present invention may be embodied on various computing platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system. The present invention may be embodied on various computing platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method for motion estimation and compensation using projection scan data, the method comprising:
   acquiring tomographic projection data of a moving object of interest;

sorting the projection data according to a phase to generate phase-sorted projection data;
loading the phase-sorted projection data;
performing an iterative optimization procedure comprising;
   changing one or more regularization parameters during the iterative optimization procedure, wherein the one or more regularization parameters affect a strength of one or more regularizers of a cost functional and wherein the one or more regularization parameters includes an optical flow constraint (OFC) strength and a volume regularization strength;
   performing a volume sub-iteration of the phase-sorted projection data using the one or more regularization parameters and the one or more regularizers of the cost functional;
   performing a motion sub-iteration of the phase-sorted projection data using the one or more regularization parameters and the one or more regularizers of the cost functional; and
repeating the iterative optimization procedure until a stopping criterion has been met.

2. The method of claim 1, wherein the strength of the OFC increases during the optimization procedure and the strength of the volume regularization decreases during the iterative optimization procedure.

3. The method of claim 1, wherein the one or more of the regularization parameters are changed non-monotonically during the iterative optimization procedure.

4. The method of claim 1, wherein the OFC strength is changed non-monotonically during the iterative optimization procedure.

5. The method of claim 1, wherein the motion sub-iteration is based on phase motion vector fields (MVF) to describe motion.

6. The method of claim 5, wherein phase MVF act between neighboring phase images and each MVF is specified on a regular grid to ensure the uniform application of the optical flow constraint.

7. The method of claim 1, wherein the motion sub-iteration is based on a global in time motion function to describe motion.

8. The method claim 1, wherein the projection data is selected from cone beam computed tomography (CBCT) projection data, dental CT projection data, clinical Computed Tomography ("CT") data, industrial CT projection data, flat panel CT (e.g., C-arms) projection data, x-ray diffraction projection data, x-ray based imaging projection data and projection data not based on x-ray imaging.

9. A method for motion estimation and compensation using projection scan data, the method comprising:
acquiring tomographic projection data of a moving object of interest;
sorting the projection data according to a phase to generate phase-sorted projection data;
loading the phase-sorted projection data;
performing an iterative optimization procedure comprising;
   performing a volume sub-iteration of the phase-sorted projection data using one or more regularization parameters and one or more regularizers of a cost functional, wherein the volume sub-iteration is based on phase motion vector fields (MVF) to describe motion, wherein the one or more regularization parameters affect a strength of the one or more regularizers of the cost functional and wherein the one or more regularization parameters includes an optical flow constraint (OFC) strength and a volume regularization strength;
   performing a motion sub-iteration of the phase-sorted projection data using the one or more regularization parameters and the one or more regularizers of the cost functional, wherein the motion sub-iteration is based on a global in time deformation function to describe motion; and
repeating the iterative optimization procedure until a stopping criterion has been met.

10. The method of claim 9, wherein one or more of the regularization parameters are changed during the iterative optimization procedure.

11. The method of claim 10, wherein the strength of the OFC increases during the iterative optimization procedure and the strength of the volume regularization decreases during the iterative optimization procedure.

12. The method of claim 10, wherein one or more of the regularization parameters changes non-monotonically during the iterative optimization procedure.

13. The method of claim 12, wherein the strength of the OFC changes non-monotonically during the iterative optimization procedure.

14. The method of claim 9, wherein the optical flow constraint (OFC) is used to regularize volume sub-iterations and wherein phase MVF act between neighboring phase images and each MVF is specified on a regular grid to ensure a uniform application of the OFC.

15. A method for motion estimation and compensation using projection scan data, the method comprising:
acquiring tomographic projection data of a moving object of interest;
sorting the projection data according to a phase to generate phase-sorted projection data;
loading the phase-sorted projection data;
performing an iterative optimization procedure comprising;
   performing a volume sub-iteration of the phase-sorted projection data using one or more regularization parameters and one or more regularizers of a cost functional, wherein the one or more regularization parameters affect a strength of the one or more regularizers of the cost functional and wherein the one or more regularization parameters includes an optical flow constraint (OFC) strength and a volume regularization strength;
   performing a motion sub-iteration of the phase-sorted projection data using the one or more regularization parameters and the one or more regularizers of the cost functional, wherein the motion sub-iteration is based on a global in time deformation function to describe motion, wherein the deformation function encodes the direction and phase of the motion of voxels in the object of interest and wherein the phase of the motion is used for motion regularization; and
repeating the iterative optimization procedure until a stopping criterion has been met.

16. The method of claim 15, wherein the strength of the OFC changes non-monotonically during the iterative optimization procedure.

17. The method of claim 15, wherein the strength of the OFC increases during the iterative optimization procedure and the strength of the volume regularization decreases during the iterative optimization procedure.

18. The method of claim 15, wherein the volume sub-iterations use motion vector fields (MVF) between phase images to describe motion.

19. One or more non-transitory computer-readable media having computer-executable instructions for performing a method of running a software program on a computing device for motion estimation and compensation of a CT image, the computing device operating under an operating system, the method including issuing instructions from the software program comprising:
  acquiring tomographic projection data of a moving object of interest;
  sorting the projection data according to a phase to generate phase-sorted projection data;
  loading the phase-sorted projection data;
  performing an iterative optimization procedure comprising;
    changing one or more regularization parameters during the iterative optimization procedure, wherein the one or more regularization parameters affect a strength of one or more regularizers of a cost functional and wherein the one or more regularization parameters includes an optical flow constraint (OFC) strength and a volume regularization strength;
    performing a volume sub-iteration of the phase-sorted projection data using the one or more regularization parameters and the one or more regularizers of the cost functional;
    performing a motion sub-iteration of the phase-sorted projection data using the one or more regularization parameters and the one or more regularizers of the cost functional; and
  repeating the iterative optimization procedure until a stopping criterion has been met.

20. The media of claim 19, wherein the strength of the OFC increases during the optimization procedure and the strength of the volume regularization decreases during the iterative optimization procedure.

21. The media of claim 19, wherein the one or more of the regularization parameters are changed non-monotonically during the iterative optimization procedure.

22. The media of claim 19, wherein the motion sub-iteration is based on motion vector fields to describe motion.

23. The media of claim 19, wherein the motion sub-iteration is based on a global in time motion function to describe motion.

24. A system for motion estimation and compensation using projection data of an imaged object of interest, the system comprising:
  a memory for storing projection data of an object of interest;
  a data processor for estimating and compensating for motion in the projection data, wherein the data processor is adapted for performing the following operations:
    sorting the projection data according to a phase to generate phase-sorted projection data;
    loading the phase-sorted projection data;
    performing an iterative optimization procedure comprising;
      changing one or more regularization parameters during the iterative optimization procedure, wherein the one or more regularization parameters affect a strength of one or more regularizers of a cost functional and wherein the one or more regularization parameters includes an optical flow constraint (OFC) strength and a volume regularization strength;
      performing a volume sub-iteration of the phase-sorted projection data using the one or more regularization parameters and the one or more regularizers of the cost functional;
      performing a motion sub-iteration of the phase-sorted projection data using the one or more regularization parameters and the one or more regularizers of the cost functional; and
    repeating the iterative optimization procedure until a stopping criterion has been met.

25. The system of claim 24 wherein the motion sub-iteration is based on motion vector fields to describe motion or on a global in time motion function to describe motion.

* * * * *